(12) United States Patent
Schweizer

(10) Patent No.: US 10,973,591 B2
(45) Date of Patent: Apr. 13, 2021

(54) OPERATING APPARATUS AND OPERATING METHOD FOR OPERATING A MEDICAL DEVICE

(71) Applicant: Hans Schweizer, Plattling (DE)

(72) Inventor: Hans Schweizer, Plattling (DE)

(73) Assignee: Siemens Healthcare GmbH, Erlangen (DE)

(*) Notice: Subject to any disclaimer, the term of this patent is extended or adjusted under 35 U.S.C. 154(b) by 203 days.

(21) Appl. No.: 15/898,166

(22) Filed: Feb. 15, 2018

(65) Prior Publication Data

US 2018/0228556 A1 Aug. 16, 2018

(30) Foreign Application Priority Data

Feb. 16, 2017 (DE) .................. 10 2017 202 517

(51) Int. Cl.
*A61B 34/00* (2016.01)
*A61B 6/00* (2006.01)
(Continued)

(52) U.S. Cl.
CPC ............ *A61B 34/25* (2016.02); *A61B 6/4405* (2013.01); *A61B 6/464* (2013.01); *A61B 6/465* (2013.01);
(Continued)

(58) Field of Classification Search
CPC ....... A61B 6/4405; A61B 34/25; A61B 90/37; A61B 90/94; A61B 2017/00207; A61B 2090/0813; A61B 2090/00818; A61B 2090/365; G06F 1/163; G06F 3/011; G06F 3/016; G06F 3/017; G06F 3/0304;
(Continued)

(56) References Cited

U.S. PATENT DOCUMENTS

2005/0128184 A1\* 6/2005 McGreevy ......... A61B 18/1206
345/156
2011/0018903 A1\* 1/2011 Lapstun ................. G02B 26/06
345/633
(Continued)

FOREIGN PATENT DOCUMENTS

CN 103402562 A 11/2013
CN 103858088 A 6/2014
(Continued)

OTHER PUBLICATIONS

European Search Report for corresponding Application No. 18152034.7—1115, dated Mar. 12, 2018.
(Continued)

*Primary Examiner* — David Tung
(74) *Attorney, Agent, or Firm* — Lempia Summerfield Katz LLC

(57) ABSTRACT

An operating apparatus for a medical device and a corresponding operating method are provided. The operating apparatus includes a projector that is configured for real, virtual, or real and virtual projection of an operator surface onto a display element, and a capture facility for non-contact capturing of an interaction of an operator with the projected operator surface. A sensor system for independent detection of the interaction is arranged separately from the capture facility on the display element.

12 Claims, 6 Drawing Sheets

(51) Int. Cl.
| | | |
|---|---|---|
| *G06F 3/01* | (2006.01) | |
| *G06F 1/16* | (2006.01) | |
| *G06F 3/03* | (2006.01) | |
| *A61B 90/00* | (2016.01) | |
| *A61B 90/94* | (2016.01) | |
| *G06F 3/042* | (2006.01) | |
| *G06F 3/0481* | (2013.01) | |
| *G02B 27/01* | (2006.01) | |
| *A61B 17/00* | (2006.01) | |
| *A61B 90/50* | (2016.01) | |
| *G06F 3/0488* | (2013.01) | |
| *G06K 19/06* | (2006.01) | |
| *G06T 19/00* | (2011.01) | |
| *A61B 34/20* | (2016.01) | |

(52) U.S. Cl.
CPC ............... *A61B 6/467* (2013.01); *A61B 6/54* (2013.01); *A61B 90/37* (2016.02); *A61B 90/94* (2016.02); *G06F 1/163* (2013.01); *G06F 3/011* (2013.01); *G06F 3/017* (2013.01); *G06F 3/0304* (2013.01); *G06F 3/0425* (2013.01); *G06F 3/04815* (2013.01); *A61B 6/4441* (2013.01); *A61B 2017/00203* (2013.01); *A61B 2017/00207* (2013.01); *A61B 2017/00216* (2013.01); *A61B 2034/256* (2016.02); *A61B 2090/0813* (2016.02); *A61B 2090/0818* (2016.02); *A61B 2090/365* (2016.02); *A61B 2090/368* (2016.02); *A61B 2090/371* (2016.02); *A61B 2090/372* (2016.02); *A61B 2090/376* (2016.02); *A61B 2090/502* (2016.02); *G02B 27/0172* (2013.01); *G02B 2027/0134* (2013.01); *G02B 2027/0138* (2013.01); *G02B 2027/0178* (2013.01); *G06F 3/016* (2013.01); *G06F 3/04883* (2013.01); *G06K 19/06075* (2013.01); *G06T 19/006* (2013.01); *G06T 2210/41* (2013.01)

(58) Field of Classification Search
CPC ............ G06F 3/04815; G06F 3/04883; G06F 3/0425; G06K 19/06075; G06T 19/006; G06T 2210/41; G02B 27/0172; G02B 2027/0134; G02B 2027/0138; G02B 2027/0178

See application file for complete search history.

(56) References Cited

U.S. PATENT DOCUMENTS

| | | |
|---|---|---|
| 2012/0211422 A1 | 8/2012 | Thys |
| 2012/0249741 A1* | 10/2012 | Maciocci ................ G06F 3/011 348/46 |
| 2013/0237811 A1* | 9/2013 | Mihailescu ........... A61B 8/4438 600/424 |
| 2013/0342350 A1* | 12/2013 | Popescu ................. G08B 21/02 340/573.1 |
| 2015/0248170 A1 | 9/2015 | Abovitz et al. |
| 2016/0307001 A1* | 10/2016 | Dow ....................... G06F 21/83 |
| 2017/0172398 A1 | 6/2017 | Carlson |
| 2018/0173323 A1* | 6/2018 | Harvey ................. G06T 19/006 |
| 2018/0228556 A1 | 8/2018 | Schweizer |

FOREIGN PATENT DOCUMENTS

| | | |
|---|---|---|
| CN | 108433823 A | 8/2018 |
| DE | 102006019864 A1 | 11/2007 |
| DE | 102012210821 A1 | 1/2014 |
| DE | 102013104429 A1 | 5/2014 |
| DE | 102014207127 A1 | 10/2015 |
| DE | 102014217559 A1 | 3/2016 |
| DE | 102015204767 A1 | 9/2016 |

OTHER PUBLICATIONS

German Office Action for German Application No. 102017202517.4, dated Sep. 15, 2017.

Chinese Office Action for Chinese Application No. 201810140251.8 dated Apr. 22, 2020.

* cited by examiner

OPERATING APPARATUS AND OPERATING METHOD FOR OPERATING A MEDICAL DEVICE

This application claims the benefit of DE 10 2017 202 517.4, filed on Feb. 16, 2017, which is hereby incorporated by reference in its entirety.

BACKGROUND

The present embodiments relate to an operating apparatus for a medical device and an operating method for operating a medical device using an operating apparatus of this type.

US 2015/0248170 A1 discloses a method and a system for providing a virtual user interface related to a totem. The user interface is created based on a detected manipulation of the totem. The virtual user interface is rendered at map points determined from a virtual world model. The map points are linked to a position of the totem, so that the user interface, when viewed by a user, appears to be stationary at the position of the totem.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an improved first-error security operation of a medical device is provided.

An operating apparatus of one or more of the present embodiments for a medical device includes a projection facility that is configured for real or virtual projection of an operator surface on a display element, as well as a capture facility for non-contact capturing of an interaction between an operator and the projected operator surface. This type of operating apparatus may already make possible improved operation of a medical device compared to conventional operation (e.g., in a sterile environment). In order also to make possible such improved operation of the medical device in situations and application cases in which first-error security is required, there is provision in accordance with the present embodiments for a sensor system separate from the capturing facility to be present on the display element for independent capturing of the interaction. In other words, there is thus provision for the interaction (e.g., an operating action of the operator) to be captured or detected in at least two ways that are independent of one another (e.g., in two different fashions). This redundant capturing or detection of the interaction results in protection against inadvertent operation or incorrect operation and/or against a misrecognition of the interaction or of an interaction. For example, in safety-relevant or safety-critical situations, this enables the safety of operations or patients to be enhanced or provided. The operating apparatus in this case makes possible operating options that, when compared to a conventional operation, based on a actuation of physical buttons or levers, for example, are especially flexible (e.g., are thus also able to be adapted dynamically or depending on the respective situation), as well as being especially clear and intuitive and especially easy to perceive. In addition, the operating apparatus of one or more of the present embodiments makes an improved adherence to requirements in relation to a sterility of a working environment or of points of contact between the operator (e.g., a doctor carrying out the treatment) and the medical device possible with far less effort.

For example, for reasons of safety, a movement of the device, which may potentially lead to a collision with a patient, may be impermissible solely by a gesture control in order to avoid endangering the patient. Thus, to enable or confirm the device movement, in addition to the operating gesture, a separate signal (e.g., a separate interaction) may be necessary.

The display element in the sense of the present embodiments is a physical, real object in the form of a panel, for example. A surface or an area of a surface (e.g., a side or side surface of the display element) forms a projection surface, on which the operating surface is displayed and/or appears at least for the operator (e.g., as viewed by the operator). The operator surface thus appears at least for the operator or from the operator's viewpoint to be superimposed on the display element. In a real projection of the operator surface, the surface may also be seen, for example, by further persons without any technical equipment. In a virtual projection, the operator surface may merely be displayed or appear, for example, virtually (e.g., apparently) on the display element and is then only visible for the operator. For this, for example, the projection facility may be a pair of smart glasses or a part of a pair of smart glasses or a comparable device. In this case, the operator surface may be displayed real (e.g., by a transparent or part-transparent element such as a viewing panel) of the projection facility or of the smart glasses such that the operator surface appears stationary at or on the display element for the operator wearing or using the projection facility. It is thus possible in the case of a virtual projection that further persons standing around may not see the operator surface on the display element, at least provided the further persons are not likewise using a corresponding projection facility.

For example, with a virtual projection of the operator surface, this thus involves an augmented-reality application (e.g., augmented-reality or mixed-reality projection). It may also be possible to project the operator surface simultaneously as a real projection and a virtual projection onto the display element. This has the advantage that the operator surface is visible both for the operator and also for further persons, who in this way, for example, may be informed especially quickly and simply by the displayed operator surface. In addition, in this way, a flexible operability of the operating apparatus by a number of persons may be realized especially simply. For this, for example, at least one further capture facility that detects an interaction of a further person with the real projected operator surface may be provided. In this case, the operator may thus interact with the virtually displayed operator surface, and the further person may interact with the real projected operator surface. In this case, a number of capture facilities may be provided. It may be possible for both the operator and also the further person to interact with the real projected operator surface, where one capture facility may then suffice. Likewise it may be possible for both the operator and also the at least one further person to each use their own projection facility (e.g., their own smart glasses), where the respective virtual projections may then be synchronized with one another. The respective virtual projections in this case represent the operator surface at an individually correct angle of view and position-dependent perspective. In this case, a good collaboration between a number of people may be improved, for example. For example, synchronized representations of the operator surface may be created on different display elements, so that a collaboration between persons that are not present in the same room is made possible. Possible fields of application of synchronized presentations of the operator surface are in the areas of telemedicine, training, or education and service.

The capture facility for non-contact capturing of the interaction may, for example, include at least one camera (e.g., a stereoscopic or 3D camera) and/or further sensors as well as at least one evaluation facility configured for processing or for evaluating corresponding camera and/or sensor data. For example, the non-contact capture may include a gesture recognition. As an alternative or in addition, the capture facility may include a sensor worn by the operator or arranged on the operator (e.g., for capturing movement and/or gestures). An acceleration and/or a position sensor may be used for this purpose, for example. Likewise, as an alternative or in addition, a capturing and/or tracking of position and/or movement (e.g., a capturing of gestures) by a radar sensor is possible. The capture facility is thus not restricted to optical and/or passive capture methods. Likewise, the capture facility may include at least one electrical sensor (e.g., an electromyography sensor). Likewise, the capture facility may include a capacitive proximity sensor, for example, by which a location, position, movement, and/or gesture of the operator is able to be captured. The capture facility or a sensor of the capture facility may be arranged on or in the display element. The use of such a sensor or of a corresponding capture facility (e.g., not dedicated to purely optical capture) may be especially advantageous precisely in the medical environment, since the operator is, for example, often not free in the selection, position, or posture (e.g., during an examination or treatment of a patient). Thus, the danger of a gesture not being captured because of an unfavorable capture angle of a camera may be minimized. In addition, such sensors may even capture the smallest movements, which may be advantageous, for example, in the often restricted space conditions in an examination or treatment situation.

The separate sensor system for independently capturing the interaction may be constructed identically or similarly to the capture facility, where the sensor system and the capture facility may then detect the interaction (e.g., a gesture of the operator) from different angles of view, observation, or detection. This enables the danger of an incorrect recognition or misinterpretation of the interaction, for example, as a result of an unfavorable perspective of the capture facility or of the sensor system for the recognition and evaluation, to be significantly reduced.

In order to keep an outlay in components or a financial outlay low, to provide the sterility of the operating apparatus as simply as possible and be able to maintain the sterility as such and to further enhance the first-error security, there is, however, provision for the capture facility and the sensor system to be based on different functional principles for capture or detection of the interaction. In this case, it is not absolutely necessary for the interaction to be captured by the capture facility and the sensor system in the same resolution or to the same degree or detail. Thus, for example, it may already be sufficient for the sensor system to be configured to capture or to detect whether the operator has interacted with the operator surface or the operating apparatus (e.g., whether any operator action has taken place at all).

At least a part of the operator surface and/or a second operator surface and/or further operator elements for the operator may be projected independently of the display element purely virtually, or at least the part of the operator surface and/or the second operator surface and/or the further operator elements for the operator may be presented in some other way. This projection or presentation may, for example, be shown virtually floating in free space. This process may also involve a hologram or a holographic projection.

In one embodiment, the display element includes an upper part and a lower part, where the lower part includes the sensor system and the upper is able to be detached from the lower part without damage and is held reversibly on the part. In other words, the display element is thus embodied in at least two parts, where both parts are able to be separated from one another. For example, the upper part that may be removed from the lower part does not have any electrics, electronics, or circuits, or at least none that are temperature-sensitive. In a medical environment (e.g., in a sterile environment), this has a decisive advantage, in that the upper part is able to be sterilized especially easily, safely, and without damaging the upper part. In one embodiment, the upper part may be formed for this purpose from an undamaged, steam-sterilizable, and/or autoclavable material (e.g., a plastic, a glass, a ceramic, or metallic material). This thus also enables the upper part to be sterilized individually (e.g., independently or separately) from the lower part and the medical device. This enables a germ-free operability of the medical device to be provided easily, since the upper part may serve as a display or projection surface for the operator surface and may thus form the only point of contact between the operator and the operating apparatus or the medical device respectively during operation. The display element (e.g., the upper part) may, for example, be the size of one of the mobile (e.g., portable) tablet computers normal nowadays. The upper part may be held on the lower part, for example, by a magnetic connection or holder. A latch, a clamp, a geometrically molded receptacle or holder, or any other type of form-fit connection may be provided for holding the upper part on the lower part.

The upper part may be adapted to the functionality of the sensor system and/or of the capture facility. The display element, for example, may be embodied entirely or partly transparent, non-conductive, and/or antimagnetic, and/or adapted with respect to corresponding reflectiveness. This enables a way in which the sensor system and/or the capture facility functions to be supported. The upper part may be embodied to let the radiation used by the sensor system arranged on the lower part (e.g., radio waves and/or Terahertz waves) pass through the upper part. The same may generally apply to the display element (e.g., even with a one-piece design).

The display element (e.g., the upper part) may have an antimicrobial coating.

The upper part, such as by a suitable thickness of material, may be embodied as stable in its form in order to simplify handling and limit the danger of damage. As an alternative, the upper part may be embodied as a film. This advantageously enables savings to be made in material, weight, and space. In addition, this enables an attenuation of the radiation used by the sensor system and/or the capture facility to be minimized. The embodiment of the upper part as films may also make possible an especially flexible arrangement. In this case, the upper part may be held by a vacuum holder.

The at least two-part design or the at least two-part construction of the display element and the arrangement of the sensor system in the lower part (e.g., arranged when operating according to specification on a side of the upper part facing away from the operator) makes it possible, for example, to dispense with covering the upper part with a sterile transparent film, as is typically used nowadays with conventional operating parts of medical devices. The ergonomics of operation and/or the ability to recognize respective operating elements are significantly restricted by this sterile covering, and the attachment of the covering demands additional, time-consuming work steps during the preparation of an operating theatre, for example. These disadvantages may be overcome by the present embodiments. Thus, for example, the medical device along with the lower part arranged on the device may be surrounded very easily with a sterile covering or envelope, while the upper part may be sterilized separately and may be held on the lower part despite the covering of the lower part. The two parts in this case may be held on one another without any problems despite the cover arranged between them. A relatively small hole in the cover, for example, through which a holder connecting the two parts may pass, may, however, be provided without this significantly endangering the sterility of the upper part or of the respective working area.

In one embodiment, the sensor system may be configured to capture the interaction using an evaluation of a touching of the display element by the operator. In other words, the operator may touch or have to touch the display element in order to carry out an interaction with the operator surface or to bring about or provide the capturing or detection of this interaction by the sensor system. This enables an inadvertent operation of the operating apparatus (e.g., based on a gesture or movement captured unintentionally by the capture facility) to be avoided. To enable the touching of the display element to be evaluated, the sensor system is configured to capture or to detect the touching. For example, the sensor system may include a sensor that senses a movement of the display element caused by the touch, a pressure on the display element exerted by a touch by the operator, and/or a change of an electrical variable, such as, for example, a capacitance, an inductance, or an electrical resistance, associated with the touch (e.g., the movement or the pressure). The sensor system may thus, for example, include as touch-sensitive sensor, a pressure sensor, a capacitive sensor, a bimetallic strip, or the like. Likewise, a number of these types of sensor may be provided.

The use of a number of sensors and/or the use of different sensors enables a redundancy for the capturing of the interaction by the sensor system to be created, whereby a reliability, a fault safety, and an operating safety of the operating apparatus may be improved. An at least two-channel measurement may be applied at a subordinate level. The sensor system or the at least one sensor of the sensor system may be arranged, for example, on a side or holder of the display elements that, for example, faces away from the operator or from a side or surface of the display element serving as a real or virtual projection surface. This enables it to be provided that this surface serving for projection is able to be safely sterilized, without damaging the sensor system. It is likewise avoided that the display of the operator surface will be restricted or adversely affected in detectability by the sensor system during a real projection.

In one embodiment, the sensor system or the at least one sensor of the sensor system may be arranged on a connection or holder between the upper part and the lower part or may be integrated into this connection or holder or form this connection or holder. This enables an especially high sensitivity for the touch to be achieved, since the corresponding pressure or the corresponding movement of the upper part has a direct effect on the sensor or is passed on via this to the lower part or is supported on the part.

In one embodiment, the operator surface is divided into a number of sectors (e.g., quadrants), where the sensor system includes a number of sensors arranged distributed and also an evaluation facility configured, by an evaluation of sensor data of the individual sensors, to determine the sector in which the interaction is taking place or has taken place. Thus, for example, the respective sensor data or sensor signals may be compared with one another in order to determine the part of the display element and accordingly the part of the operator surface with which the operator is interacting or has interacted. This enables the first-error security of the operating apparatus to be further improved, since the sensor system may now not only capture whether an interaction has taken place at all, but, for example, which of a number of different functions is to be initiated by the interaction or in which sector, segment, or part area of the operator surface and/or of the display element the interaction has taken place. Thus, in this way, a more precise reconciliation between the interactions detected by the capture facility and by the sensor system is made possible, whereby possible discrepancies may be recognized with a higher degree of detail (e.g., with improved accuracy).

For example, there may be provision for a pressure sensor to be arranged in each case in four corner areas of the display element. Then, if the operator touches the display element in one of these corner areas, the pressure sensor arranged there will measure a relatively high pressure, while, for example, a pressure sensor arranged diagonally opposite the sensor will measure a relatively low pressure. For a touch in a central area of the display element, which is at an equal distance from all four pressure sensors, all four pressure sensors will measure an at least essentially equal pressure. In this manner, from a comparison of the sensor data of a number of sensors, a position at which the operator is touching the display element may be established (e.g., at which the interaction is taking place or has taken place). It may be recognized in this way by the sensor system, with which function (e.g., with which part or which operating element of the operator surface) the operator has interacted if each sector is assigned exactly one function or one operating element.

A number of functions may be assigned to one or more sectors of the operator surface. In one embodiment, in such cases, similar functions (e.g., functions that are similar as regards content, subject matter, or with regard to effect on the medical device or a patient) are bundled or collected into one sector in each case. Each sector may thus be assigned a specific class or category of functions. This enables it to be made possible to provide in an especially reliable manner that the interaction captured by the capture facility, at least with respect to the category or class of the corresponding function, matches the interaction captured by the sensor system.

As an alternative, it may be advantageous to assign similar functions to different sectors. This enables an especially precise identification and thus also insurance against a misrecognition of the interaction by the capture facility (e.g., when similar gestures are provided for initiating these similar functions).

The user or operator surface may be subdivided or constructed in accordance with a predetermined grid, so that, for example, individual operating elements will always be displayed at predetermined positions or relative positions. In addition, the display element may have physically molded groove patterns, raised sections, recesses, flutings and/or other surface features that may likewise be aligned to the predetermined grid or arrangement pattern of the virtual or projected operating elements of the operator surface. In this manner, a respective operator may only physically touch or feel virtual or projected displayed operating elements or functional areas of the operator surface, whereby an especially safe and reliable operation may be made possible.

In one embodiment, the sensor system is combined with an actuator system that is configured, as a reaction to an interaction (e.g., captured by the sensor system), to create a haptic signal at the display element. In other words, a haptic feedback may thus be communicated, through which the respective operator may recognize especially precisely and reliably whether the respective operator has successfully carried out the interaction or whether the interaction has been successfully captured. This may be advantageous, for example, with functions that do not have immediately visible effects that thus relate, for example, to a control of invisible radiation.

It is precisely in a medical environment that the creation of the haptic signal may be especially advantageous, since the respective operator is often wearing gloves, whereby a tactile perception capability may possibly be restricted. It may be possible, for example, to create a vibration of the display element (e.g., of the upper part) as a haptic signal. In order to give even clearer and more distinct haptic feedback to the respective operator, there may be provision, depending on the function actuated or depending on the interaction or type of interaction captured, for creating a different haptic signal. The haptic signal may thus be created as a function of the interaction. This thus enables the respective operator to receive immediate feedback as to whether the respective operator successfully operated or initiated the desired function in each case. Different haptic signals may, for example, differ in length, frequency, a temporal pattern, or a strength or amplitude.

In one embodiment, the projection facility includes a Head-Mounted Display (HMD) (e.g., an augmented-reality headset).

The term "projection facility" is to be broadly defined in the sense of the present embodiments and is intended to refer to a facility that is suitable and is configured for displaying the operator surface. This display does not absolutely have to involve a projection in the strict sense of the word. Likewise there may be provision, for example, for at least a part area of a sight glass of the HMD to be embodied, for example, as a transparent or part-transparent screen. Likewise, a coupling-in of light serving to display the operator surface may be provided, for example, via one or more optical waveguides.

The use of an HMD is advantageous, since a freedom of movement and action of the operator is not restricted by the device. In addition, it can be provided by the use of the HMD in conjunction with the operating apparatus of one or more of the present embodiments that all functions and operating elements needed are available in a single place, which makes especially simple, fast, and efficient operation possible. By a projected (e.g., ultimately electronically created) operator surface, for example, only a selection of functions and operating elements needed for the situation concerned may be displayed. Thus a restricted size of the display element does not effectively represent any limitation, since all possible functions or operating elements do not have to be accessible (e.g., displayed) at the same time.

In one embodiment, a plurality of further operating options are made possible by the use of the HMD, which are able to be used precisely in a sterile environment for non-contact operation (e.g., of medical devices). There may be provision that, for example, likewise by the capture facility, the device to be operated in each case is recognized and uniquely localized in the room. A 3D camera may be used for this purpose, for example. This may be part of the HMD, arranged thereon, or be arranged separately therefrom, on a wall or a ceiling of the respective room, for example. By an arrangement on or as part of the HMD, the device to be operated in each case may be located in the field of view of the operator. This enables there to be a dynamic adaptation of the operator surface and/or the operating functions or operating gestures available, since these may be tuned in each case to the device to be operated located in the field of view of the operator. An arrangement of the capture facility and/or of a further facility (e.g., of the 3D camera) on a fixed-position facility (e.g., the wall or ceiling of a room) may make it possible to capture both the operator and also all operated devices especially well, without this resulting in any perspectives being concealed.

The actuator system of the sensor system or a further actuator system may be arranged entirely or partly in or on the HMD. This enables a haptic signal to an operator's head to be created. The arrangement in or on the HMD may make possible an especially simple embodiment of the display element and, in doing so, also make haptic feedback possible. This arrangement may also be advantageous, since the arrangement is made possible by this for a number of persons, who are each using their own HMD, to transfer the haptic signal. In this way, a number of persons may thus simultaneously follow and verify respective operating actions of the operator, whereby collaboration and/or training may be improved, for example. Also in this way, an immersion of participants at remote locations in a process communicated in each case by augmented or virtual reality may be improved.

In an embodiment, the display element may include a machine-readable code (e.g., a QR code) that specifies a type of the display element. The operating apparatus is then configured to read this code (e.g., to capture and evaluate the code), for which, for example, the capture facility may also be able to be used. The projection facility is then configured to select the operator surface to be projected as a function of the type of the display element from a plurality of predetermined different operator surfaces. In other words, a physical marking is thus provided on the display element, which makes possible a recognition or identification of the display element and/or of one or more characteristics of the display element by the operating apparatus. The type of the display element may be determined by one or more characteristics of the display element. For example, this may include a size, an intended purpose for which the display element is to be used and/or place of use, a specification of the respective sensor system, a color, and/or more. Likewise, it may be specified by the code, for example, where (e.g., on which device) the display element is located (e.g., the device for the operation of which the display element is provided). Through the use of such an explicit and dedicated machine-readable code, the recognition and identification of the display element as such by the operating apparatus may be supported or improved. In addition, the operator surface or the corresponding display may be adapted precisely and reliably to the respective display element as a function of the code or as a function of the data encoded by the code. This is possible clearly when the code encodes the size and color of the display element or of a surface of the display element intended for presenting the operator surface. For example, a position of this surface relative to the position of the code may be encoded or communicated by this. By evaluation of the code, the operator surface may be scaled adapted in the optimum way to the respective display element and also adapted with respect to a color scheme used, in order to provide an optimum display and recognizability.

As an alternative to a QR code, other codes such as, for example, a pattern of holes, a bar code, or the like may also be used.

Likewise, the code may, for example, encode a software license or a corresponding usage permission for a software product and/or a device or point to corresponding data respectively. The latter might be done by encoding an address of a corresponding data record on a license server. In this way, there may thus be provision, for example, for the operator surface to only include or make accessible the functions and/or operating elements enabled by the respective license or permission.

The code may be exchangeable. For example, there may be provision for the operator or a corresponding user to create the code (e.g., the QR code) themselves and/or attach the code to the display element themselves. The code may, for example, be glued on, held magnetically, or by clamping, or be screwed on. The operator may thus, for example, create the code or the QR code with computer support and then print the code out, for example, and glue the code to the display element.

In one embodiment, a layout and/or a selection of functions of the operator surface may be encoded by the code. This provides the option of the operator surface or at least a characteristic of the operator surface being able to be individually predetermined by the operator. Thus, the operator, such as by an editor, may, for example, determine a choice and arrangement of operating elements and/or a color of the operator surface in accordance with requirements. In one embodiment, these types of configurations in this case may be created in advance and be changed especially quickly and by exchanging the code on the presentation device. This may be done, for example, during a treatment without an unsterile operating device possibly having to be used in this process.

A machine-readable code of this type may, for example, also be attached to or arranged on the device to be operated in each case, whereby a recognition, identification, and localization of the device or of specific subelements of the device is supported. Thus, for example, the operation of the device by gestures and corresponding gesture recognition may be improved, in that, in addition to the gestures, the data contained in the respective code or codes is evaluated, used, or taken into account in the interpretation or evaluation of the gestures. This makes possible an especially reliable operation of devices, without the devices having to be touched (e.g., without unsterile parts of the respective device having to be touched).

In order to improve this type of non-contact operation of devices with respect to the first-error security and in doing so at the same time to design the operation to be especially simple and convenient and flexible, a sequential use of the different operating options or operating channels available (e.g., the independent capturing of the respective interaction or interactions) may be provided. In other words, for example, initially by a non-contact interaction (e.g., an operating gesture), a function or function sequence to be carried out may thus be selected or predetermined. This will then subsequently be confirmed or enabled by interaction with the display element (e.g., sterile display element; by touching the display element and only then actually transferred to the device or carried out by the device).

The enabling or confirmation may likewise be done by another initiation facility (e.g., by a foot switch). The facility does not necessarily have to be sterile in this case. There may thus then be provision, for example, initially by an operating gesture (e.g., maintaining a sterility) for predetermining a function (e.g., a movement into a required or target position). Subsequently, this function predetermined by the operator will be initiated by actuating the initiation facility and actually implemented. The use of methods of augmented and/or virtual reality enables a virtual model (e.g., avatar) of the medical device to be operated to be projected or displayed, for example. This virtual model may then be moved by the operator, using corresponding operating gestures, into the target position. This method enables possible conflict or contact points to be recognized even before the real movement, for example. Likewise, unnecessary real device movements or position corrections may be avoided, whereby a mechanical load or stress on the device is minimized.

A two-stage or sequential sequence of operating steps with initially a purely virtual predetermination, subsequent enabling, and only then real implementation of the predetermination taking place is also advantageous, since during the predetermination of the function to be carried out, an individual enabling of individual functions, subfunctions, or function steps may be omitted. This enables savings to be made in a number of necessary operating actions for reaching a result and an operating efficiency to be increased as well as enabling an unnecessary restriction on the operator to be avoided.

Likewise, in reverse order, by interaction with the display element, a specific function, function sequence, or group of functions may be enabled. Then, interaction (e.g., non-contact interaction) with the operator surface or by corresponding gestures may be actually given, specified, or carried out. The first-error security may be further improved by this sequential sequence. In addition, in this manner, it may be avoided that the respective person is restricted in a scope or a complexity of possible operating actions, since the operating gestures for capture by the capture facility and touching the display element for capture by the sensor system thus do not have to be carried out simultaneously.

In a further embodiment, the display element may be provided as a single-use component. This provides that the display element is configured to only be used once. For example, the display element may by packed under sterile conditions by the manufacturer and be unpacked for use (e.g., in a sterile working environment). This also enables the advantage of operation not impeded by an additional covering, foil, or envelope to be realized. At the same time, with this solution, the display element may, however, have temperature-sensitive components (e.g., electronic or electrical circuits), a magnetic holder, an actuating system for creating the haptic signal, actual buttons for a precise and detailed operability, and/or more. The display element may then likewise have a communication module for wireless data transmission, whereby a flexible ability to arrange the display element in the working environment is made possible. The display element may thus be flexibly positioned so that it is possible for the operator to reach the display element and operate the display element in a flexible manner at all times. The wireless data transmission may be directed, for example, directly to the device to be operated or to another element of the operating apparatus, such as, for example, a data processing facility for evaluation of the detected interactions and/or for generating a control signal for the device to be operated as a function of the captured interactions.

In an embodiment of the display element in two or more parts, only an upper part intended to be actually touched by the operator may be provided as a sterile packed single-use part, for example, while, for example, a lower part able to be used permanently or multiple times may serve as a receiving station for receiving the data transmission emanating from the operating or upper part. This enables an outlay in materials and money for using the operating apparatus to be minimized.

In a further embodiment, the interaction with the display element may be undertaken using a mobile operating element. The mobile operating element may be a stylus, for example, by which the respective operator may interact with the projected operator surface by touching the display element with the stylus, for example, and/or by the stylus being guided along the display element. This contact is captured by the sensor system and is followed if necessary. This enables a more precise operation to be made possible. It is thus possible for the operator only to be in direct touch contact with the mobile stylus, so that if necessary, sterility may be provided. This enables the sterility of the working environment to be provided with especially little effort. An input element of this type enables specific interactions or operating instructions to be undertaken easily and precisely (e.g., if lines, outlines, trajectories, movement paths, or more are to be displayed or drawn).

An operating method of one or more of the present embodiments serves to operate a medical device using an operating apparatus (e.g., using an operating apparatus of one or more of the present embodiments). In order to make possible a first error safe operation of the medical device, an operator surface for the medical device may, for example, be projected as a real or virtual surface on a display element of the operating apparatus. If an operator interacts with this projected operator surface, this interaction is captured in a non-contact manner. In addition, the interaction is detected independently of the non-contact capturing of the interaction. A control signal for the medical device is then generated by the operating apparatus as a function of the captured and detected interaction and is transferred to the medical device.

In one embodiment, a plausibility check may be carried out by the operating apparatus of respective results of the capture characterizing the interaction, such as by the capture facility, and of the detection, such as by the sensor system of the interaction. The control signal for the medical device is only transferred to the device when the result of the plausibility check is that the two results are plausible in relation to one another. Depending on the embodiment of the operating apparatus, it may be determined by the plausibility check, for example, whether the captured interaction corresponds to the detected interaction and/or whether the capturing and the detecting have occurred simultaneously or, for example, within a predetermined period of time in relation to one another.

The capture facility and/or the sensor system may be configured to capture a temporal sequence of a number of interactions and/or of parts of an interaction and evaluate the interactions (e.g., with respect to a plausibility). Thus, it may be that not only an actuation (e.g., a click or a touch) will be captured, but also, an approach that has occurred previously (e.g., of a hand, of a finger, and/or of an operating object) to the display element and/or to a predetermined room volume that is intended for carrying out operating actions (e.g., operating gestures). If such an approach preceding the actuation or operating action is not captured, then an incorrect initiation may be concluded if necessary. By taking into account a temporal sequence, a safety bonus and improved reliability may thus be achieved.

The operating method may be carried out, for example, by the operating apparatus or by using the facilities explained in conjunction with the operating apparatus.

The characteristics and developments of the operating apparatus and also of the method specified previously and below, and the corresponding advantages are in each case able to be transferred analogously in both directions between the operating apparatus and the operating method. This also applies to the components or facilities used or to be used for carrying out the method. For this reason, there will not be any explicit formulation provided here of each aspect both for the operating apparatus and also for the operating method.

DETAILED DESCRIPTION

Figure 1:
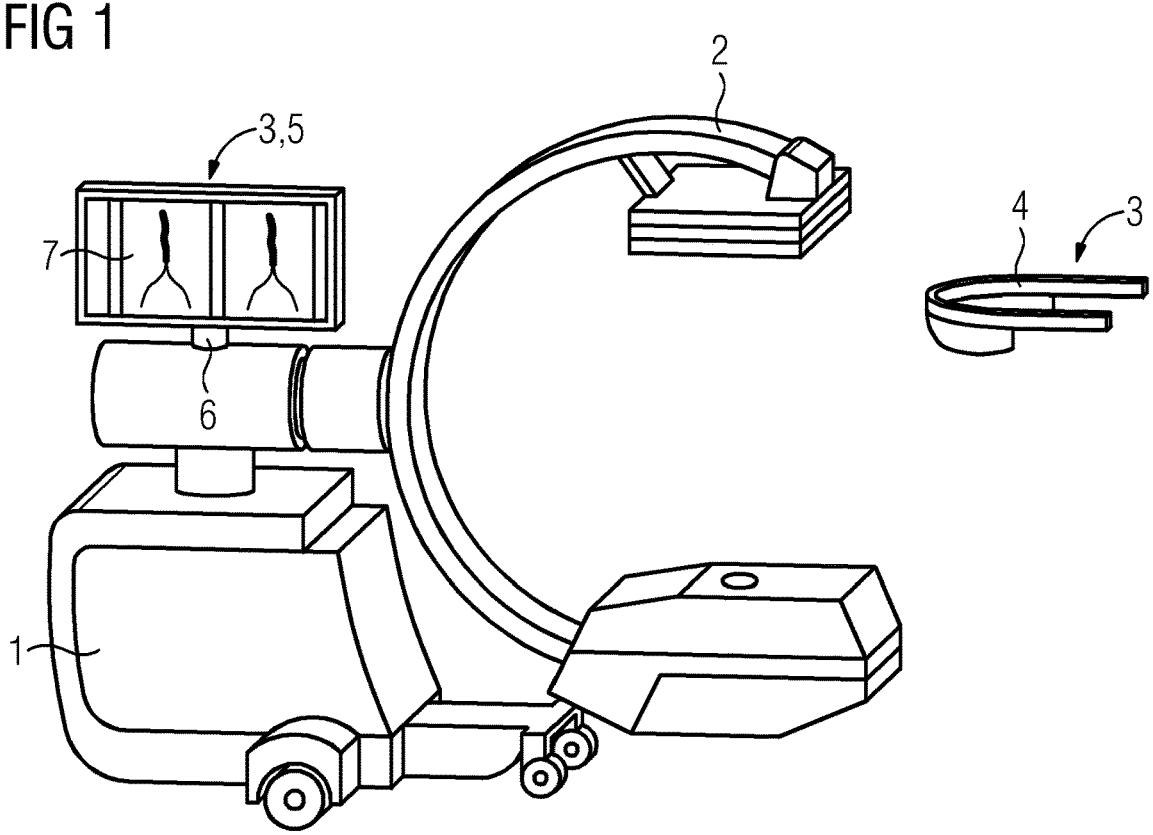
FIG. 1 shows a schematic perspective view of one embodiment of a medical device with a schematically indicated operating apparatus.

Elements that are the same, have the same functions, or correspond to one another are labeled in the figures with the same reference character in each case.

FIG. 1 shows a schematic diagram of one embodiment of a medical device 1 that includes a mobile x-ray device with a C-arm 2.

Medical devices often have a plurality of functions, functionalities, mechanical degrees of freedom, and correspondingly numerous and complex operating elements at their disposal. In such cases, it has previously been the universal practice for these devices and corresponding diversity of functions to be operated via operating elements that are arranged at different points on the respective device. This provides that disadvantageously a respective operator, who is standing and working right next to the C-arm 2, does not have all functions available to the respective operator within easy reach. In this case, devices, such as the mobile x-ray device shown, in operating theatres or for intraoperative applications, will thus, for example, be used in sterile environments. In such cases, the problem emerges of the operator often not being able to operate all the possible functions without at least in some cases leaving the sterile area. Also, concealment of operating elements, displays, or monitors (e.g., by parts of the medical device 1 or by further bystanders) may be problematic at least for specific functions or applications (e.g., an adjustment of an collimator or the like). Overall, the problem thus emerges, in this type of demanding environment, of creating a possibility for operating complex devices that allows an ergonomic operation of the complex functions, meets the requirements for a sterile operability, and also offers a first-error security (e.g., in accordance with Standard IEC6060-1).

In order to address these problems, there is provision in the present embodiments for the medical device 1 to be operated by an operating apparatus 3 shown schematically in FIG. 1. The operating apparatus 3 in the present example includes a projection facility in the form of a pair of smart glasses 4 and also a display element 5 that is arranged on, for example, the medical device 1. The operating apparatus 3 may also include further elements not shown explicitly here. The display element 5 is connected to the medical device 1 via, for example, a connection 6 (e.g., a holder, receptacle, or support).

The smart glasses 4 may be an augmented-reality headset, for example, and may, for example, include one or more 3D or depth-sensing and RGB cameras for capturing the environment, projection elements for stereoscopic imaging, a movement sensor (e.g., head tracking), and a data processing unit. In addition, a loudspeaker and/or a microphone may, for example, be provided as part of the smart glasses 4 or the operating apparatus 3, through which, for example, assistive operation by voice control or voice commands may be made possible. Thus, using the smart glasses 4, the respective environment, including the medical device 1 and the display element 5, may be captured. Likewise, operating gestures of the operator that are carried out, for example, in empty space or, for example, directly at or in front of the display element 5 may be captured. Using the smart glasses 4, an assignment may be made between real spatially localized objects, such as the medical device 1 and the display element 5, and a virtual environment or virtual objects or representations. Thus, the smart glasses 4 make virtual, augmented, or mixed reality possible for the operator by using functions and operating actions. The data processing unit may also be arranged separately from the smart glasses in this case, for example, in the form of a stationary computer system.

The smart glasses 4 thus form, if necessary in conjunction with a further camera not shown here, for example, a capture facility for non-contact capturing of an operating action of the operator. In the present case, there is provision for an operator surface to be projected virtually onto the display element 5, so that the operator surface 7 thus appears for the operator wearing the smart glasses 4 on or at the display element 5. As the operator sees it, the operator surface 7 thus appears in a fixed location relative to the display element 5. In this case, the operator surface 7 is displayed with the correct perspective in each case at a respective position and adapted to a respective angle of view of the operator relative to the display element 5.

In the present case, there is provision for the display element 5 to be formed in two parts, from an upper part and a lower part, for example. The lower part is connected to the medical device 1 on a side facing away from the operator, while the upper part includes a display surface 10 facing towards the operator (cf. FIG. 2), which is used for the projection (e.g., virtual if necessary) of the operator surface 7 or as a corresponding background for the operator surface 7. In one embodiment, the upper part of the display element 5 is formed by an element able to be sterilized by steam without damaging the element (e.g., a panel-shaped element). This may then be released from the lower part and thus also from the medical device 1 and individually safely sterilized. The lower part includes, for example, a sensor system, by which contact with the display element 5 (e.g., pressure thereon) and/or a resulting movement of the display element 5 or of the upper part, is able to be detected. The sensor system may include a pressure sensor, for example, that may be arranged, for example, in or on the connection 6 and/or between the upper part and the lower part (e.g., at a respective point of contact between the lower part and the upper part).

The operator surface 7 may, for example, include or display a number of individual operating elements that correspond to appropriate functions of the medical device 1. In addition or as an alternative, data such as, for example, medical image data, x-ray images, endoscopy data, and the like may also be displayed as part of the operator surface.

The operator is presented before his or her eyes by the operating apparatus 3, via the incorporation of the operator surface (e.g., by the stereoscopic display facility of the smart glasses 4), with the user surface 7 not really physically present on the display element 5, with which, however, the operator may still interact. The interaction (e.g., an operating action such as an operating gesture) is captured in this case both by the capture facility (e.g., the gesture capture of the smart glasses 4) and also by the sensor system provided on the display element independently and based on different functional principles. If the operator thus undertakes this type of interaction or operating action for operation or control of the medical device 1, by making a corresponding gesture, then this is captured by the operating apparatus 3 and converted into a corresponding control signal for the medical device 1 depending on the type of captured interaction or operating action. This is then transferred to the medical device. In this case, there is provision for the medical device 1 just to be controlled in accordance with the captured interaction if the interaction captured by the capture facility and the interaction detected by the sensor system correspond to one another or are plausible in relation to one another. By this process, an inadvertent operation is advantageously avoided, and thus, first-error security is achieved.

The operating action or interaction may, for example, be the touching of a specific subarea of the display element 5 assigned to a specific function of the medical device 1. This provides that, for example, an operation of virtually displayed operating knobs, buttons, slide controls and the like is still possible. In order, for example, to be able to use complex operating actions or gestures for operation of the medical device 1, there may also be provision for corresponding function or functions or instructions predetermined by one or more gestures only to be carried out after they have been enabled. This may be done, for example, by physically touching the display element 5 and/or by a further operating, enabling, or initiating element (e.g., a foot switch).

Figure 2:
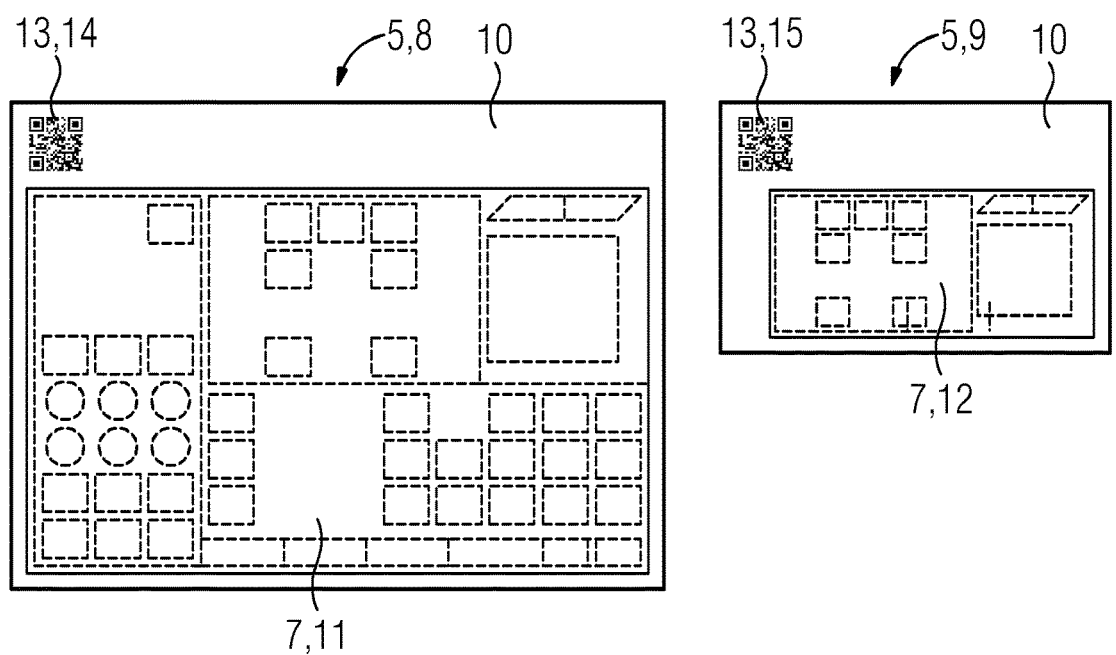
FIG. 2 shows a schematic overhead view of two different exemplary display elements.

FIG. 2 shows a schematic overhead view of two different types of display element 5. A large display element 8 and a small display element 9 are shown. In the present example, the large display element 8 and the small display element 9 differ, for example, with respect to size. Accordingly, an expanded operator surface 11 with a plurality of individual operating elements or functional areas that may not be displayed on the small display element 9 may be shown on the large display element 8. Therefore, in the present example, a restricted operator surface 12 with an alternate choice and arrangement of operating elements or functional areas is shown on the small display element 9. The restricted operator surface may, for example, be scaled smaller than the expanded operator surface 11 and/or be simplified or reduced in functions in relation to the unit. The operator surfaces 11, 12 are thus adapted in each case to the size of the display element 8 or to the small display element 9.

To enable this adaptation to be carried out reliably and in an automated manner, the display elements 8, 9 each have a machine-readable code 13 that may be captured, read out, and evaluated, for example, by the capture facility of the operating apparatus 3. In the present example, the code 13 involves a QR code that encodes a respective individual type (e.g., a size) of the respective display element 8, 9. The large display element 8 includes, for example, a code 14 that has at least one characteristic of the large display element 8 as data content. Accordingly, the small display element 9 in the present example includes a code 15 that has at least one characteristic of the small display element 9 as data content. The remaining display elements 5, shown in the other figure, for example, may have such individually machine-readable codes 13.

The codes 13 make possible or facilitate a unique capturing and identification of the respective display element 5 or 8, 9 even under difficult conditions in order to achieve a reliable projection or display of the projected operator surface 7, 11, 12. In this case, a spatial (e.g., horizontal or vertical) alignment of the respective display element 5 may also be specified by the code 13, for example. These types of code 13 may also be employed for the use of more than one display element 5 simultaneously and still make a unique assignment identification possible. Thus, for example, even with a perspective change and/or if one of the display elements 5 is concealed, it may be provided that the intended operator surface 7, 11, 12 will always be displayed on a specific display element 5.

Figure 3:
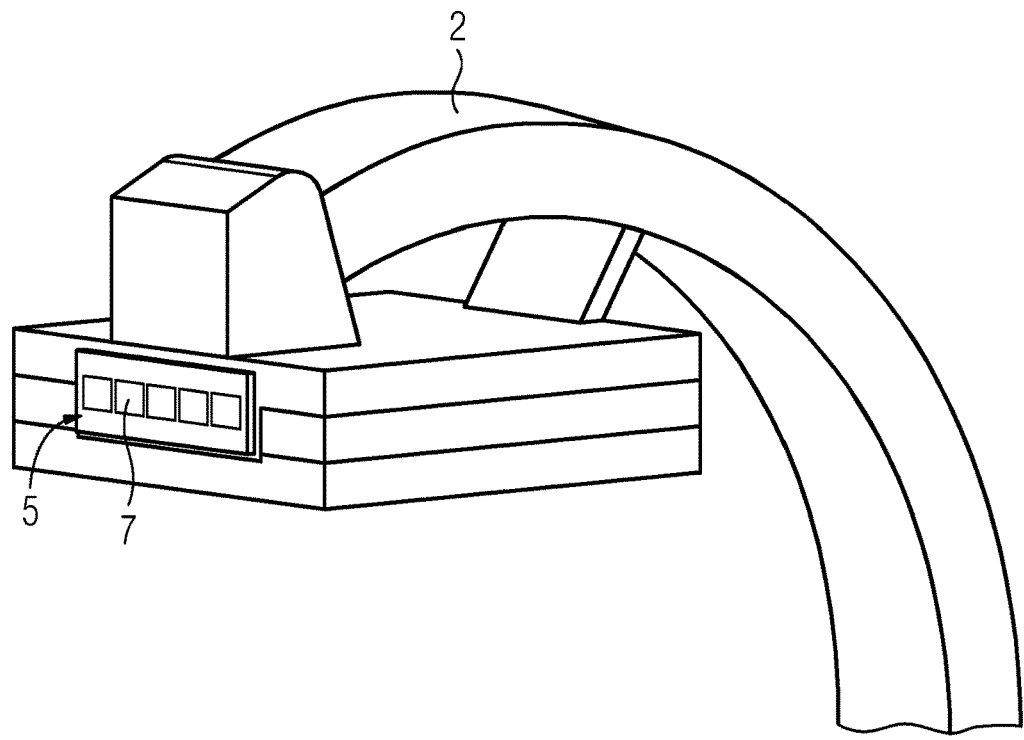
FIG. 3 shows a schematic and sectional perspective view of a further medical device with an exemplary display element arranged thereon.

FIG. 3 shows a schematic and sectional diagram of one embodiment of a C-arm 2 with a flat-panel detector, on which a display element 5 is arranged. Also shown schematically is an operator surface 7 adapted to the shape and size of the display element 5. Thus, a further example of an application is illustrated by this figure.

Figure 4:
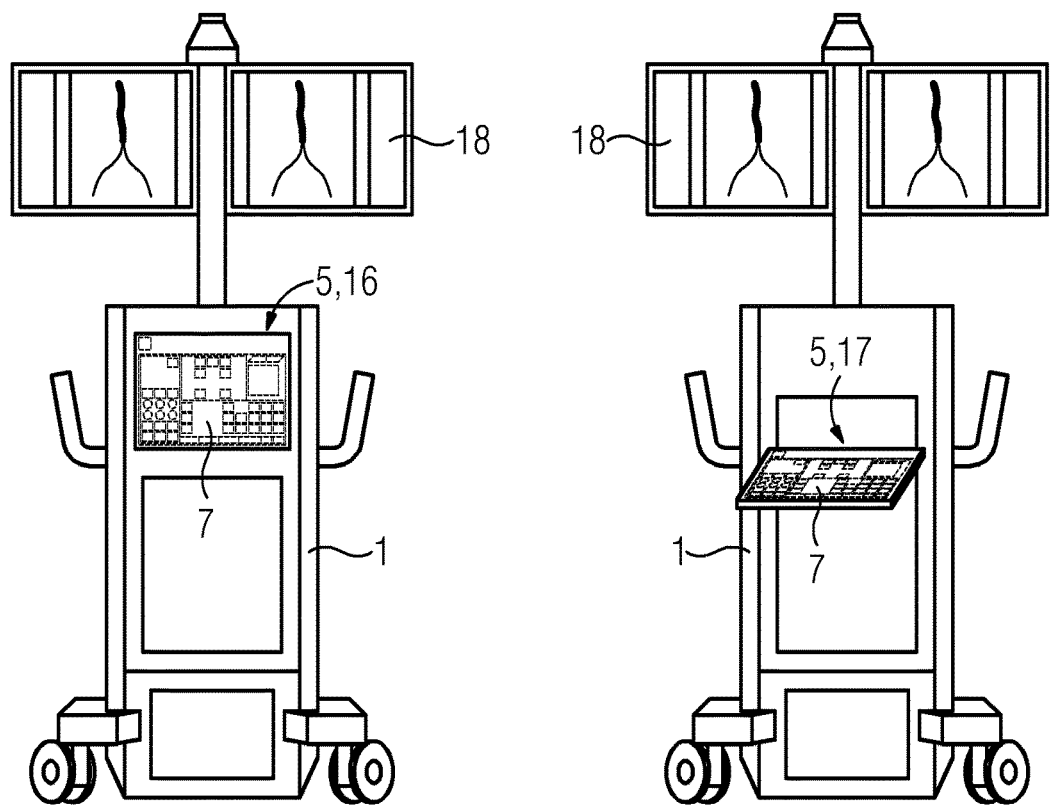
FIG. 4 shows a schematic diagram of a further medical device with an exemplary display element arranged thereon in two different positions.

FIG. 4 shows a further schematic diagram of a medical device 1 that in the present example involves a monitor trolley. In the present example, a display element 5 is arranged on the monitor trolley that in the left-hand part of the diagram is arranged in a first position 16 and in the right-hand part of the diagram is arranged in a second position 17. The display element 5 may thus, for example, be able to be folded or hinged between these two positions 16, 17. This advantageously enables the position, arrangement, or alignment of the display element 5 to be adapted or set in line with the situation or requirements. In the present example, the monitor trolley includes at least one conventional screen 18 that is able to be used, for example, to display medical data or images.

Since the available monitor surface of the monitor 18 is always restricted in each case, as a result of the particular flexibility of the operating apparatus 3, the display element 5 may also be used advantageously for displaying such image material. A switch may thus be made, for example, in line with demand between such a display of medical or other image data and the display of the operator surface 7. With a purely virtual projection or display on the display element 5 for different persons, who are each using their own smart glasses 4, there may be a different display, adapted in line with demand in each case. Thus, for example, the display element 5 may be used by a first operator for display or as a projection surface or projection plate for an operator surface 7, while the display element 5 may be used simultaneously by a second operator, for example, for virtual display of an x-ray image or the like. Thus, a multiple use of the display element 5 is made possible especially advantageously by this.

In this way, the display element 5 may also serve, for example, as a support for further operating personnel as a display surface if, for example, a view of the dedicated screen 18 is restricted in each case for these personnel.

In a corresponding manner, the display element 5 or a further display element 5 or a plurality of further display elements 5, for example, may also be arranged or held on a pull-out arm or a mount on the medical device 1, on the C-arm 2, and/or, for example, on a wall or a ceiling of a respective room.

Figure 5:
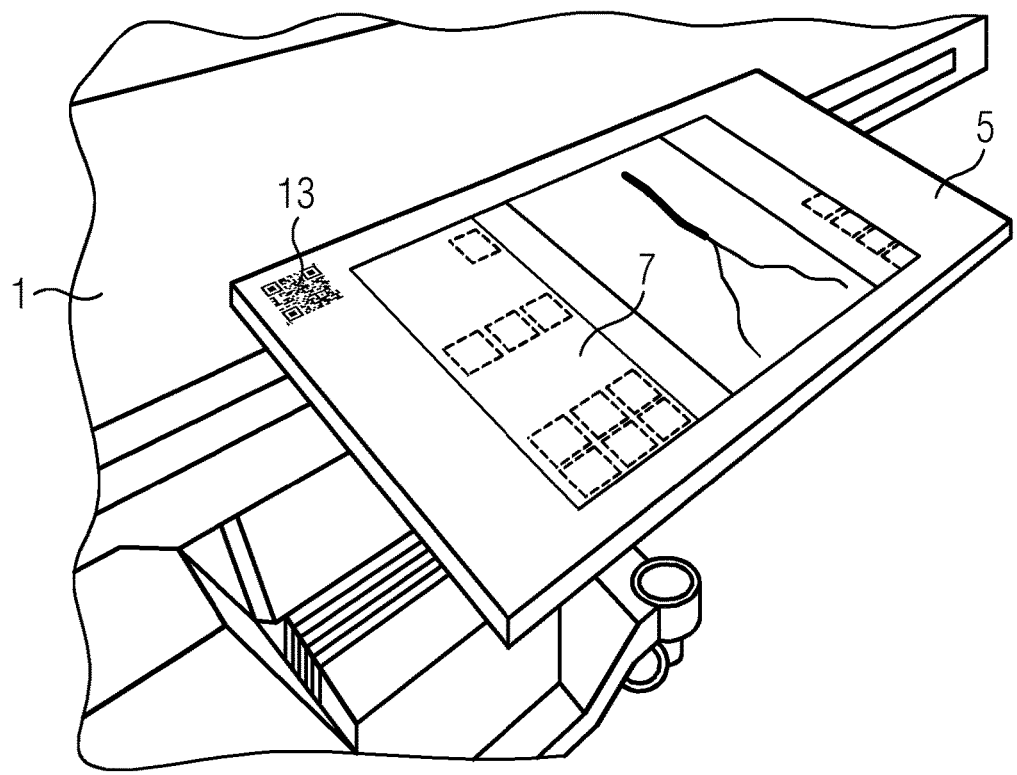
FIG. 5 shows a schematic and sectional diagram of a further medical device with an exemplary display element arranged thereon.

FIG. 5 shows, in a schematic and sectional diagram, a further example of a medical device 1 with a display element 5 arranged thereon. In the example shown here, the medical device 1 involves a patient couch or an operating table.

Figure 6:
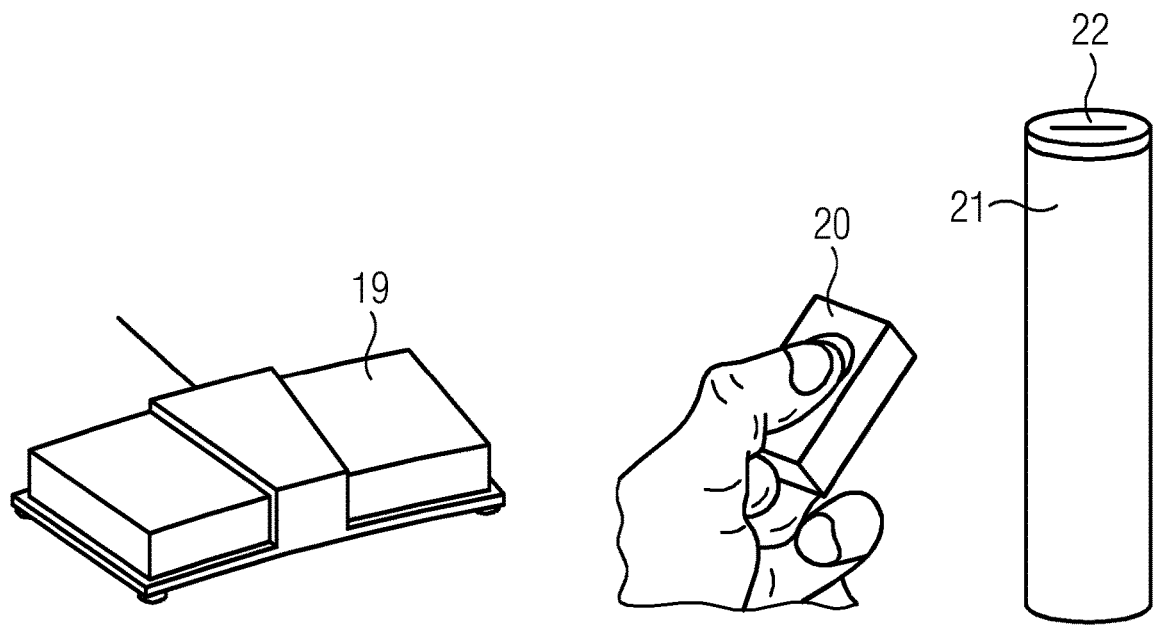
FIG. 6 shows a schematic diagram of various exemplary operating facilities for realizing multi-channel, first error safe operation.

FIG. 6 shows a schematic overview diagram of three examples of realizations of additional operating facilities. By such additional operating facilities, for example, in especially safety-critical situations or for especially safety-critical functions or function initiations, a separate enabling or confirmation may be undertaken by the operator, so that two-channel or multi-channel operation is made possible or is provided. An actuation of these additional operating facilities in each case may create an enabling or consent signal that is transferred to the operating apparatus 3 or to a data processing device of the operating apparatus 3.

There may be provision, for example, that a function of the medical device 1 will only be initiated if, at the same time as or in parallel with the corresponding operating action, such a consent signal is created by one of the additional operating facilities or is received from the operating facility 3. A predetermined time delay that lies at a maximum between the respective operating action and the associated consent signal (e.g., may elapse between the two) may also be defined. If within this predetermined period of time in relation to a time of the respective operating action no corresponding consent signal is received, the control signal corresponding to the action is not transferred to the medical device 1, providing that the corresponding function is thus not initiated.

A foot pedal 19, a manually-operated push-button 20, and also a cylinder 21 with an enabling button 22 are shown by way of example in this figure. The push-button 20 may include a dead-man's switch, for example, that, for operating or carrying out safety-critical functions, is to be held permanently in an actuated or pressed state. The push-button 20 and the cylinder 21 may be embodied as hand-held transmitters, where the respective enabling or consent signal may be sent wirelessly, for example.

Figure 7:
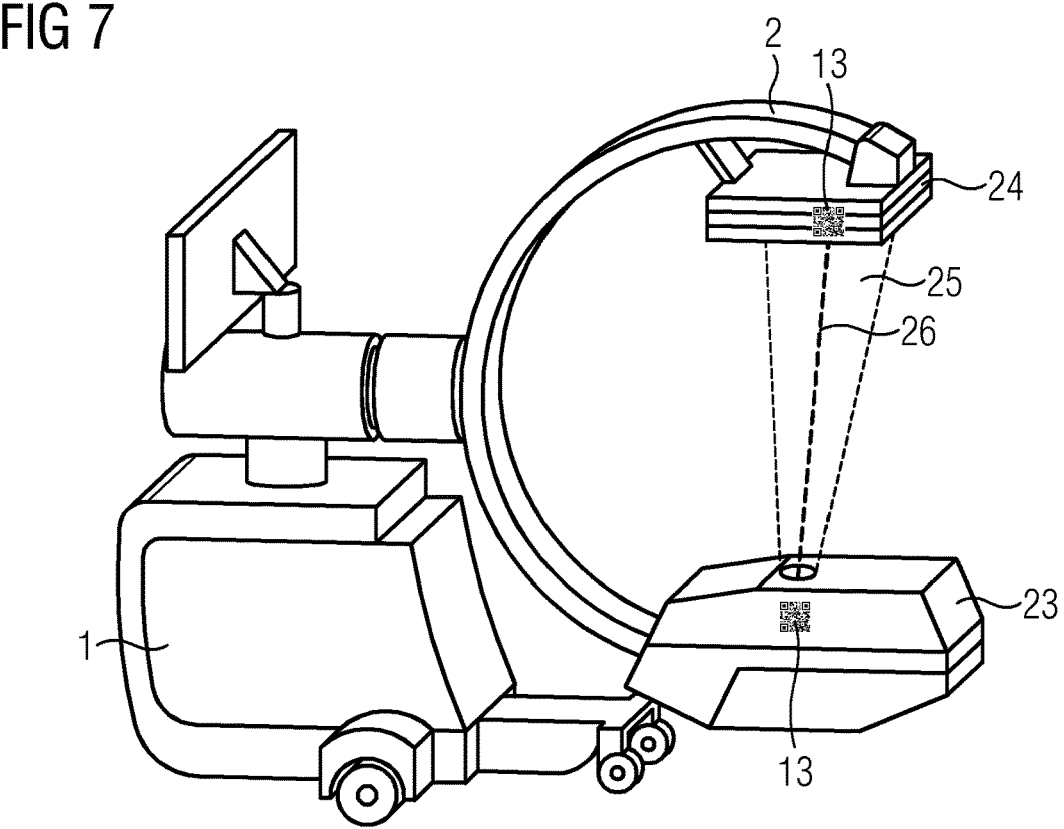
FIG. 7 shows a schematic perspective diagram of a medical device with an exemplary virtually visualized beam cone.

FIG. 7 shows a schematic perspective diagram of a medical device 1 that essentially corresponds to the device already shown in FIG. 1. The medical device shown in FIG. 7 thus involves a mobile x-ray device with a C-arm 2, on which a radiation source 23 and a detector 24 arranged opposite the source are held. Both the radiation source 23 and the detector 24 each have at least one machine-readable code 13 that is able to be read by the capture facility. Using the codes 13 of the radiation source 23 and of the detector 24, a unique identification and localization of the C-arm 2 in the room may be achieved especially simply and reliably by the operating apparatus 3. For example, when the C-arm 2 is partly concealed and/or the illumination is unfavorable, this may facilitate identification and localization and thus organize in a more reliable way.

As an alternative or via assistance, the localization and/or identification of the C-arm 2 or of the medical device 1 may be carried out, for example, by image or pattern recognition, by surface scanning, if necessary with the addition of a reconciliation with a volume model, or the like.

The codes 13 may be arranged at a known predetermined point of the radiation source 23 and the detector 24, whereby an especially precise incorporation or superimposition of virtual elements is facilitated. Physically real and virtual elements, as seen by the operator, are arranged consistently relative to one another.

In this figure, a beam cone 25 is indicated by way of example, which is shown as a virtual element, since the spatial location of the C-arm 2 relative to the smart glasses 4 worn by the operator has at least been initially established. The beam cone 25 is invisible in reality since the beam cone 25 may, for example, involve the path of radiation of the x-ray radiation emitted from the radiation source 23. The beam cone 25 is shown in this figure as a perspectively correct stereoscopic virtually projected truncated pyramid between the radiation source 23 and the detector 24. The actual or real shape of the beam cone 25 may depend on a collimator used (e.g., round or rectangular), so that the term "beam cone" is subject to a broad interpretation and is not intended to be restricted to geometrical cone shapes.

In addition, a central beam 26 of the beam cone 25 is shown in the present figure. The central beam 26 may be visualized, for example, as a line and serve as a reference object for operating gestures. Even a non-interactive display of the beam cone 25 and/or of the central beam 26 may serve to add value for a respective operator, since invisible radiation will be made at least virtually visible and thereby become especially clear (e.g., in a spatial relation with regard to an examination object). For example, this enables a correct alignment of the C-arm 2 relative to the examination object to be made easier, where positioning lasers used as an alternative may be dispensed with. In such cases, a positioning laser may not penetrate the examination object, so that the passage of the central beam 26 may only be recognizable on one side of the examination object. By contrast, the virtual display of the beam cone 25 and of the central beam 26 are advantageously not restricted by these types of physical circumstances.

In one embodiment, the beam cone 25 may be augmented by further data, and may be displayed, for example, as a function of a radiation intensity and/or as a function of a spatial distribution of a direct and a scattered radiation with a corresponding color trace or the like. This enables an unnecessary radiation load on the examination object to be minimized or avoided. The beam cone 25 may be adapted, for example, as a function of a previously set radiation dose to be used and/or as a function of a previously set spectrum to be used (e.g., likewise by a corresponding coloring). This type of especially easily recognizable adaptation of the display of the beam cone 25 reliably enables a corresponding incorrect setting to be avoided.

The superimposition or incorporation in this case is not restricted to the beam cone 25. For example, the C-arm 2 and/or other parts of the medical device 1 may also be superimposed on data and visualizations. For example, this enables a characteristic, such as, for example, a current temperature of a radiation generator, to be visualized and communicated especially clearly and rapidly, even perceptible with peripheral vision.

FIGS. 8 to 11 each shown a schematic perspective diagram of the medical device 1 from FIG. 7, where various non-contact interaction options for operation by a hand 27 of the operator indicated in each case are illustrated.

Figure 8:
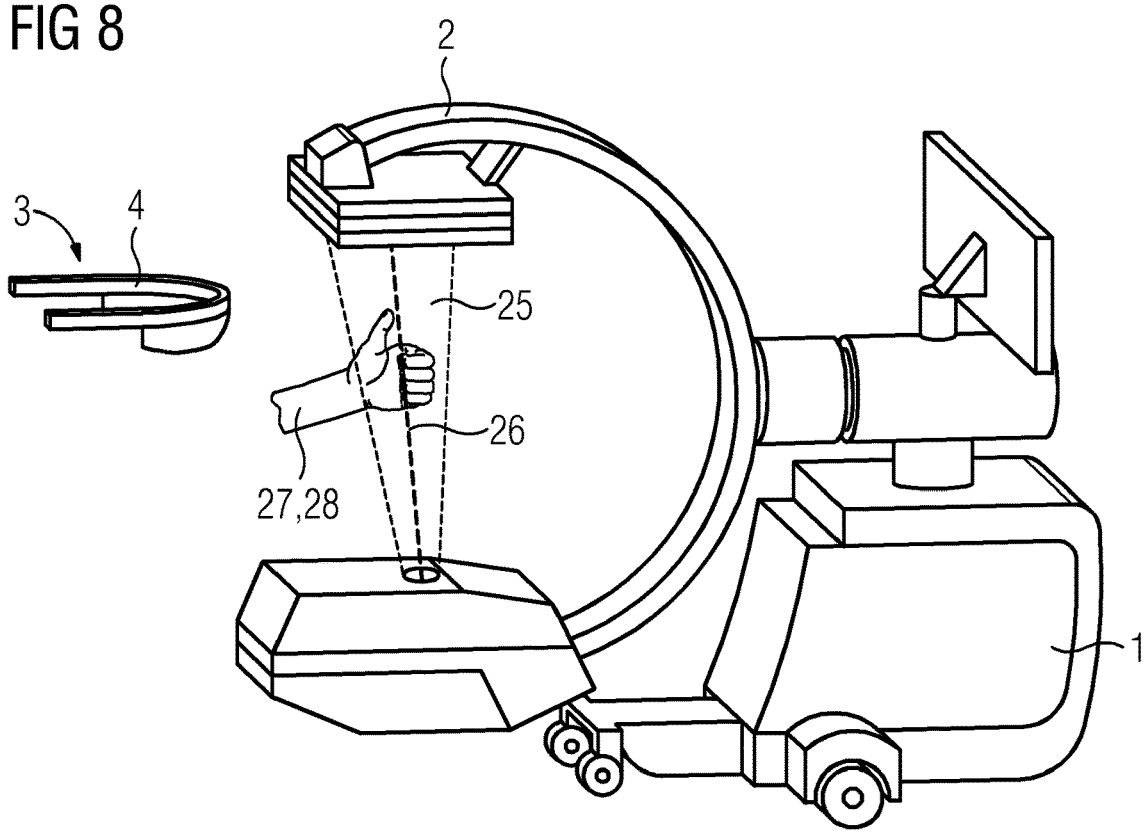
FIG. 8 to FIG. 11 show schematic perspective diagrams of the medical device from FIG. 7 with schematic illustrations of various exemplary non-contact interaction options.

In FIG. 8, a first gesture 28, through which by grasping and pulling the virtually displayed central beam 26, the C-arm 2 may be moved and aligned, is indicated. A rotation of the hand 27 may also be used, so that a movement of the C-arm 2 in accordance with all angular, orbital, and translational degrees of freedom of the C-arm 2 is made possible. The corresponding gestures may be implemented in reality, for example, by respective motor drives of the medical device 1. The operator thus does not have to touch the medical device 1 to operate the medical device 1.

Figure 9:
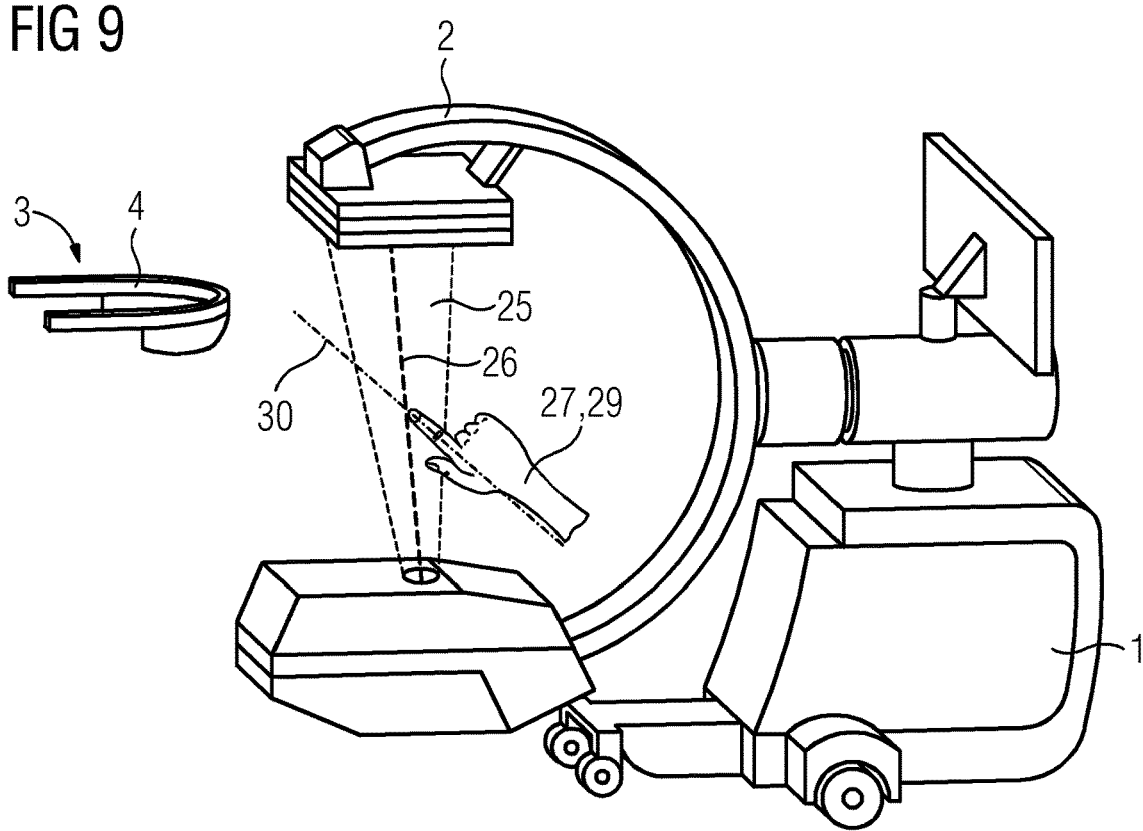

FIG. 9 indicates a second gesture 29, by which the operator, by pointing in a particular direction 30, may predetermine a new alignment of the C-arm 2. In this case, by predetermining or showing the pointing direction 30, the C-arm 2 may be caused to move in an automated manner such that the central beam 26 coincides with the pointing direction 30. Through the second gesture 29, the operator may also point, for example, to a region of interest (ROI) to be examined, which will then be brought, by adjusting the C-arm 2, into coverage with the beam cone 25. Likewise, by the second gesture 29, a new vector for the central beam 26 or a new region of interest or target region may be predetermined. This may then be stored in a list or database and retrieved for future examinations. In this way, for example, in a simple manner, even complex movements or sequences of different individual examinations with different fluoroscopy directions may be predetermined in a precise and clear manner. If necessary, this may also be carried out in the absence of the examination object and thus without the restriction of movement.

The gestures 28, 29 represent examples of gestures that may be especially clearly supported or made easier by the use of the cylinder 21. Thus, for example, the cylinder 21 may have a sensor system by which a precise spatial alignment is captured and may be transferred to the operating apparatus 3. In addition or as an alternative, the cylinder 21 may, if necessary, be captured and followed especially simply and reliably by the capture facility of the operating apparatus 3. The cylinder 21 provides the operator in this case with a physically grippable representation, for example, of the central beams 26, through which a precise alignment is made easier. Thus, in this case, a long axis of the cylinder 21 may be used as a representation or reference object or reference direction for the central beam 26. Likewise, the long axis of the cylinder 21 may also be used to predetermine the pointing direction 30 or may be captured or interpreted as the pointing direction 30. In one embodiment, the cylinder 21 may have an actuation system for creating a haptic signal. An especially precise operation or control of the medical device 1 is likewise made easier by this. For example, a recognized operating gesture may be confirmed on the part of the operating apparatus 3 by a corresponding haptic signal or corresponding haptic feedback (e.g., a vibration), and/or the reaching of a specific position or angular setting may be signaled by this type of haptic signal.

Figure 10:
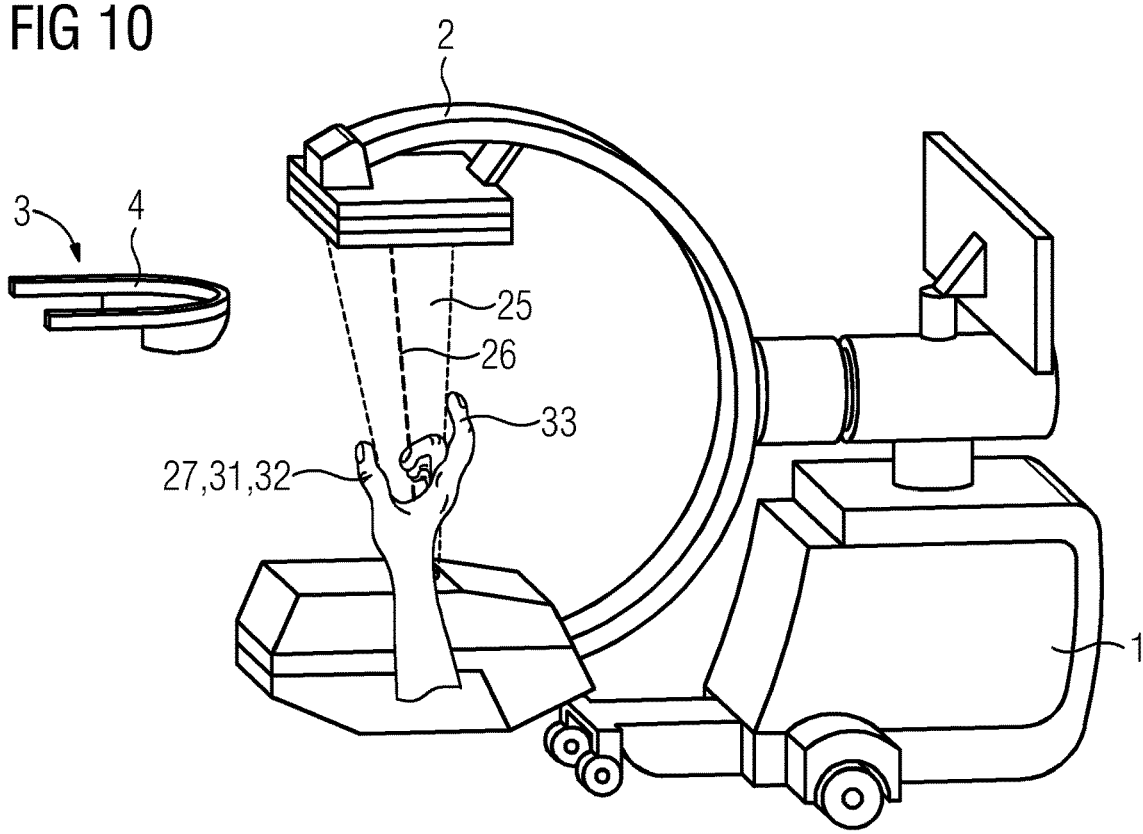

In FIG. 10, a third gesture 31, in which, for example, a first finger 30 and a second finger 33 may be moved towards one another or away from one another in order to adapt a breadth or width of the beam cone 25, which thus effectively provides a setting of a beam collimator of the beam source 23, is indicated.

Figure 11:
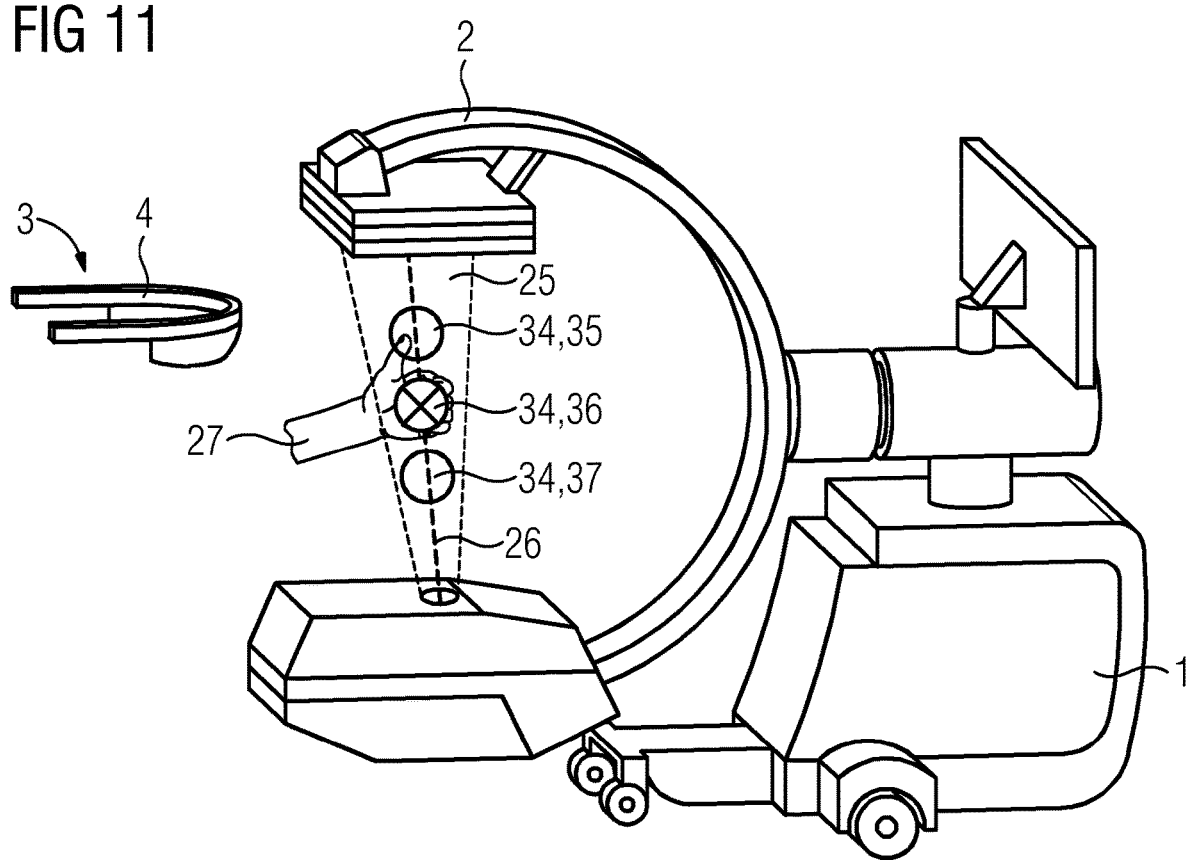

In FIG. 11, an alternative or expansion of the first gesture 28 is indicated schematically. In this case, there is provision for auxiliary operating elements 34 to be incorporated purely virtually. For example, the operator, by a corresponding operating gesture (e.g., by virtually pressing one of the auxiliary operating elements 34) may block specific movement axes of the C-arm 2 or select a specific type of movement. This may then be specified in scope by a subsequent interaction (e.g., by a dragging gesture).

For example, it may be possible, exactly and exclusively to control a vertical lift of the C-arm 2, in that the corresponding operating gesture is started with a point of departure from the virtual position of a first auxiliary operating element 35. Accordingly, for example, an operating gesture made or started at the virtual position of a second auxiliary operating element 36 may serve exclusively to cause an isocentric orbital rotation of the C-arm 2 or, for example, a linear sideways movement of the entire medical device 1 along an operating table. A third auxiliary operating element 37 may be actuated, for example, or may serve as a point of departure for an operating gesture, by which an angular rotation of the C-arm 2 is caused or is undertaken. Thus, through these types of auxiliary operating elements 34, for example, a restriction of degrees of freedom of the C-arm 2 or of the medical device 1 may be undertaken or set especially advantageously, whereby an especially precise, reliable, and safe operation and control as well as an especially reliable recognition or interpretation of the respective operating gestures is made easier.

The described examples show how, by an innovative man-machine interface based on virtual projection or augmented reality, operability and clinical workflow may be simplified, and innovative display options used and the sterility of the operating element may be provided during this process.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An operating apparatus for an x-ray device, the x-ray device comprising a radiation source and a detector, the operating apparatus comprising:
    a projector configured for real, virtual, or real and virtual projection of an operator surface onto a display element;
    a capture facility configured for non-contact capturing of an interaction of the operator with the projected operator surface, wherein the x-ray device is configured to be operated or controlled by the captured interaction of the operator with the projected operator surface;
    a sensor system configured to independently capture the interaction, the sensor system being arranged on the display element and being separate from the capture facility;
    a processing facility configured to enable the x-ray device to be operated or controlled by the captured interaction of the operator with the projected operator surface by the capture facility based on the independent capture of the interaction by the sensor system, such that the independent capturing of the interaction by the sensor system enables the capturing of the interaction by the capture facility to operate or control the x-ray device, and
    a plurality of machine-readable codes, wherein each of the radiation source and the detector comprise a respective machine-readable code of the plurality of machine-readable codes, each respective machine-readable code being readable by the capture facility to allow for identification and localization of the radiation source and the detector with respect to an operator of the x-ray device.

2. The operating apparatus of claim 1, wherein the display element comprises a machine-readable code of the plurality of machine-readable codes that specifies a characteristic of a type of the display element, the characteristic being predefined by the operator,
    wherein the operating apparatus is configured to read the machine-readable code, and
    wherein the projector is configured to select the operator surface to be projected as a function of the characteristic of the type of the display element from a plurality of predetermined different operator surfaces.

3. The operating apparatus of claim 2, wherein the machine-readable code is a QR code.

4. The operating apparatus of claim 2, wherein the characteristic of the type of the display element includes a size, a position, a spatial alignment, a selection of functions, a color, an intended use, or any combination thereof.

5. The operating apparatus of claim 2, wherein the machine-readable code is associated with a license or usage permission for a product, device, or product and device, and
    wherein the operator surface only allows access to functions, operating elements, or functions and operating elements that are enabled by the license or usage permission.

6. The operating apparatus of claim 2, wherein the machine-readable code is removably connected to the display element.

7. The operating apparatus of claim 1, wherein the capture facility is configured to capture the interaction of the operator with the projected operator surface prior to the sensor system capturing the interaction, such that the capturing of the interaction by the sensor system enables the prior capturing of the interaction by the capture facility to operate or control the x-ray device.

8. The operating apparatus of claim 1, wherein the sensor system is configured to capture the interaction prior to the capture facility capturing the interaction of the operator with the projected operator surface, such that the capturing of the interaction of the operator with the projected operator surface by the capture facility is enabled to operate or control the x-ray device by the prior capturing of the interaction by the sensor system.

9. The operating apparatus of claim 1, wherein the respective machine-readable codes of the radiation source and the detector further allow for localization of the radiation source and the detector of the x-ray medical device with respect to each other, an environment surrounding the x-ray device, or combinations thereof.

10. The operating apparatus of claim 1, wherein the respective machine-readable codes are QR codes.

11. The operating apparatus of claim 1, wherein the respective machine-readable codes are arranged at respective predetermined positions on the radiation source and the detector, and wherein an incorporation or superimposition of a virtual element is facilitated by the respective predetermined positions.

12. The operating apparatus of claim 11, wherein the virtual element is a beam cone, the beam cone comprising a central beam, and wherein the capture facility is configured to capture a non-contact interaction of the operator with the beam cone, the central beam, or the beam cone and the central beam to allow for movement or alignment of the x-ray device.

* * * * *

UNITED STATES PATENT AND TRADEMARK OFFICE
CERTIFICATE OF CORRECTION

PATENT NO. : 10,973,591 B2  
APPLICATION NO. : 15/898166  
DATED : April 13, 2021  
INVENTOR(S) : Hans Schweizer Page 1 of 1

It is certified that error appears in the above-identified patent and that said Letters Patent is hereby corrected as shown below:

In the Claims

Claim 9 (Line 61):
"and the detector of the x-ray medical device with respect to"
Should be replaced with:
"and the detector of the x-ray device with respect to"

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*